United States Patent [19]

Meilland

[11] Patent Number: Plant 6,281

[45] Date of Patent: Sep. 13, 1988

[54] ROSE PLANT—MEIBALBIKA VARIETY

[75] Inventor: Marie-Louise Meilland, Antibes, France

[73] Assignee: The Conard-Pyle Company, West Grove, Pa.

[21] Appl. No.: 895,490

[22] Filed: Aug. 11, 1986

[51] Int. Cl.[4] ..... A01H 5/00

[52] U.S. Cl. ..... Plt./1

[58] Field of Search ..... Plt. 1

*Primary Examiner*—James R. Feyrer

*Attorney, Agent, or Firm*—Burns, Doane, Swecker & Mathis

[57] ABSTRACT

A new and distinct variety of shrub rose plant is provided which forms attractive semi-double blossoms having excellent color persistence which are carmine pink suffused with a scarlet blush on the edges. Plants of the new variety are particularly floriferous in the springtime and form attractive orange fruit in the autumn. Exceptionally good disease resistance also is exhibited. The new variety is well adapted for growing in the landscape.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) of the new variety was the Meigurami variety. The male parent (i.e., the pollen parent) of the new variety was a plant formed by crossing the Curiousa variety by the City of Leeds variety. The parents of the new variety are non-patented in the United States. The parentage of the new variety can be summarized as follows:

Meigurami × (Curiosa × City of Leeds).

The seeds resulting from the above pollination were sown and 86 plantlets were obtained which were physically and biologically different from each other. Selective study resulted in the identification of a single plant of the new variety.

It was found that the new variety of shrub rose plant of the present invention possesses the following combination of characteristics:

(a) forms attractive semi-double blossoms having an excellent color persistence which are carmine pink suffused with a scarlet blush on the edges,
(b) is particularly floriferous in the springtime,
(c) forms attractive orange fruits in the fall,
(d) is exceptionally disease resistant,
(e) exhibits a propensity to readily undergo asexual propagation from cuttings, and
(f) is particularly well suited for growing in the landscape.

The new variety meets the needs of the horticultural industry for all uses. It can be grown to advantage as an attractive ornamentation in parks, gardens, public areas, and residential landscapes.

The characteristics of the new variety have been found to be homogeneous and stable and are strictly transmissible by asexual propagation from one generation to another.

The new variety has been named the Meibalbika variety.

BRIEF DESCRIPTION OF THE PHOTOGRAPH

The accompanying photograph shows, as nearly true as it is reasonably possible to make the same in a color illustration of this character, typical specimens of plant parts of the new variety. The rose plants of the one variety described herein were approximately three years of age and were grown outdoors during September on *Rose froebelii* understock at Cannet des Maures, Var, France.

DETAILED DESCRIPTION

Figures 1, 2, 3, 4, 5, 6, 7, 8, 9, 10, 11, 12, 13, 14, 15:
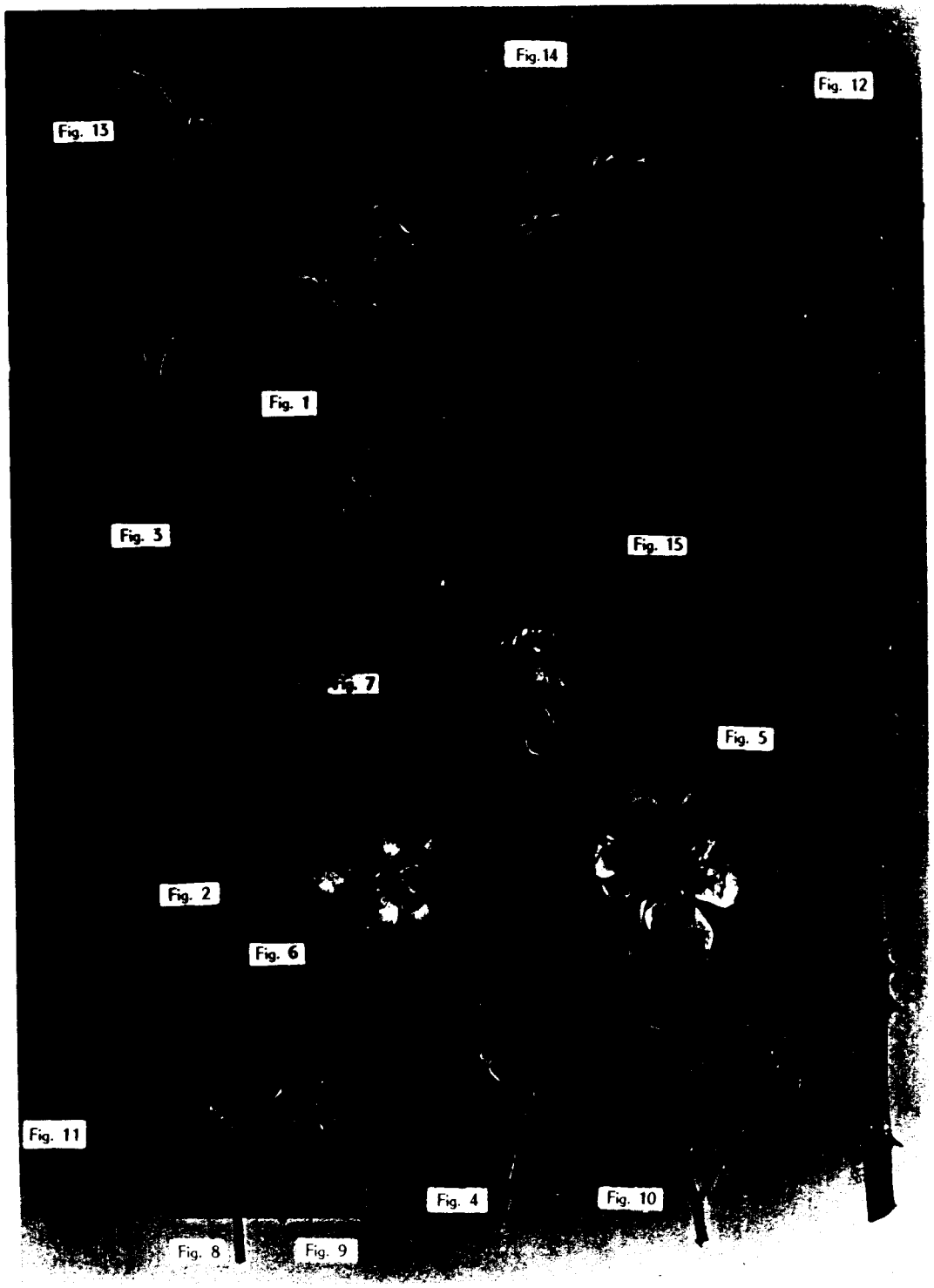
FIG. 1 illustrates a specimen of a young shoot.
FIG. 2 illustrates a specimen of four flowering buds wherein in one instance the sepals have opened.
FIG. 3 illustrates a specimen of a flowering bud at the opening of the sepals.
FIG. 4 illustrates a specimen of a flowering bud as the petals open.
FIG. 5 illustrates a specimen of a flower in the course of opening.
FIG. 6 illustrates a specimen of a fully open flower—plan view—reverse.
FIG. 7 illustrates a specimen of a fully open flow immediately prior to petal drop—plan view—obverse.
FIG. 8 illustrates a specimen of a floral receptacle showing the arrangement of the stamens and pistils.
FIG. 9 illustrates a specimen of a floral receptacle showing the arrangement of the pistils (stamens removed)
FIG. 10 illustrates a specimen of two fruits.
FIG. 11 illustrates a specimen of a flowering stem.
FIG. 12 illustrates a specimen of a main branch.
FIG. 13 illustrates a specimen of a leaf with three leaflets—upper surface.
FIG. 14 illustrates a specimen of a leaf with five leaflets—upper surface.
FIG. 15 illustrates a specimen of a leaf with seven leaflets—under surface.

The chart used in the identification of colors is that of The Royal Horticultural Society (R.H.S. Colour Chart). The terminology preceding the numbered references had been added to designate in common terms the corresponding colors. The description is based on threeyear old specimens of the new variety during September while budded on *Rosa froebelii* understock and grown outdoors in a nursery at Cannet des Maures, Var, France.

Class: Shrub.

Plant:

*Height.*—Approximately 1 meter on average.

*Habit.*—Bushy.

Branches:

*Color.*—Young stems: light green, Yellow-Green Group 146B, somewhat shaded with reddish tones. Adult wood: bronze green, Yellow-Green Group 146A.

Leaves:

*Petioles.*—Upper surface: grooved, reddish-brown on young foliage, medium green on adult foliage, edges are more or less glandular. Under surface: bronze green on young foliage, light green on adult foliage, commonly some small inconspicuous thorns are present as well as a few glands.

*Leaflets.*—Number: 3, 5 (most often), and 7. Shape: oval to lanceolate, rounded base, and acute apex. Serration: simple and regular. Texture: leathery. Color (young foliage): upper surface: dark green, Yellow-Green Group 136A, somewhat tinged with red. Under surface: medium green, Yellow-Green Group 147B, more or less spotted with red. Color (adult foliage): upper surface: dark green, Yellow-Green Group 136A. Under surface: medium green, Yellow-Green Group 147B.

Inflorescence:

*Number of flowers.*—Approximately 1 to 25 blossoms per floral stem.

*Peduncle.*—Straight, rigid, somewhat spotted with red, slightly glandular, commonly with several small thorns.

*Buds.*—Shape: oblong. Length: approximately 1.9 cm. on average. Color: upper surface: Red Group 50A, somewhat suffused on the edges with strawberry red, Red Group 46B. Under surface: Red Group 46B.

*Flower.*—Form: semi-double. Diameter: approximately 8.5 cm. on average. Color (when opening begins): upper surface: carmine pink, Red Group 52B, somewhat suffused on the edges of the external petals with claret pink, Red Group 50A. Under surface: crimson, Red Group 52A, somewhat suffused on the edges of the external petals with cardinal red, Red Group 53B. Color (when partially open): upper surface: carmine pink, Red Group 52B, somewhat suffused on the edges of the external petals with crimson, Red Group 52A. Under surface: neyron pink, Red Group 55B, somewhat suffused on the edges of the external petals with cardinal pink, Red Group 53D. Color (at end of opening): upper surface: carmine pink, Red Group 52D, somewhat suffused on the edges of the external petals with neyron pink, Red Group 55A. Under surface: neyron pink, Red Group 55B, somewhat suffused on the edges of the external petals with Red Group 58B. Fragrance: none. Petal form: rounded with a cuneiform base. Petal number: approximately 17 on average. Stamen number: approximately 113 on average. Anthers: light ochre yellow bordered with ochre. Pistils: approximately 62 on average.

Development:

*Blossoming.*—Particularly floriferous in the springtime.

*Disease resistance.*—Exceptionally good.

I claim:

1. A new and distinct variety of shrub rose plant characterized by the following combination of characteristics:

(a) forms attractive semi-double blossoms having an excellent color persistence which are carmine pink suffused with a scarlet blush on the edges, (b) is particularly floriferous in the springtime, (c) forms attractive orange fruits in the fall, (d) is exceptionally disease resistant, (e) exhibits a propensity to readily undergo asexual propagation from cuttings, and (f) is particularly well-suited for growing in the landscape;

substantially as herein shown and described.

* * * * *